United States Patent
Matusch

(10) Patent No.: US 8,075,515 B2
(45) Date of Patent: Dec. 13, 2011

(54) DISPOSABLE INJECTOR WITH AT LEAST ONE COMPRESSION BAR AND A CLOSURE CAP

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 23 days.

(21) Appl. No.: 12/592,380

(22) Filed: Nov. 24, 2009

(65) Prior Publication Data

US 2010/0076379 A1     Mar. 25, 2010

Related U.S. Application Data

(63) Continuation-in-part of application No. PCT/EP2008/004949, filed on Jun. 19, 2008.

(30) Foreign Application Priority Data

Jul. 6, 2007 (DE) .......................... 10 2007 031 714

(51) Int. Cl.
*A61M 5/30* (2006.01)
*A61M 5/20* (2006.01)

(52) U.S. Cl. ............................ 604/68; 604/72; 604/135

(58) Field of Classification Search .................... 604/68, 604/71, 72, 131, 134, 135–137
See application file for complete search history.

(56) References Cited

U.S. PATENT DOCUMENTS

| | | | | |
|---|---|---|---|---|
| 3,556,100 A | * | 1/1971 | Hurschman | 604/138 |
| 4,227,528 A | * | 10/1980 | Wardlaw | 604/139 |
| 4,378,015 A | * | 3/1983 | Wardlaw | 604/137 |
| 5,599,309 A | | 2/1997 | Marshall et al. | |
| 6,258,068 B1 | | 7/2001 | Kirchhofer et al. | |
| 2001/0039394 A1 | * | 11/2001 | Weston | 604/72 |
| 2006/0264830 A1 | | 11/2006 | Hommann | |
| 2008/0051700 A1 | | 2/2008 | Schuster et al. | |
| 2008/0146997 A1 | | 6/2008 | Hoffmann | |

FOREIGN PATENT DOCUMENTS

EP     1 336 419 A     8/2003

OTHER PUBLICATIONS

US Patent Documents continued from above: US 4,968,306 A—Date: Nov. 6, 1990, Name: Eberhardt Schluter, et al.

* cited by examiner

*Primary Examiner* — Nicholas D Lucchesi
*Assistant Examiner* — Leah Stohr
(74) *Attorney, Agent, or Firm* — R. S. Lombard; K. Bach

(57) ABSTRACT

A disposable injector with a housing that has at least one compression hook, which has at least one support surface respectively in the region of its free end. A piston-actuating plunger rests on the support surface. The locking position of the compression hook is secured by an actuating element positioned in a locked position. The actuating element has a locked position, in which it rests securely on a sealing cap. The actuating element has a triggering position, which effects lateral retreat of the compression hook when the piston-actuating plunger is released.

23 Claims, 5 Drawing Sheets

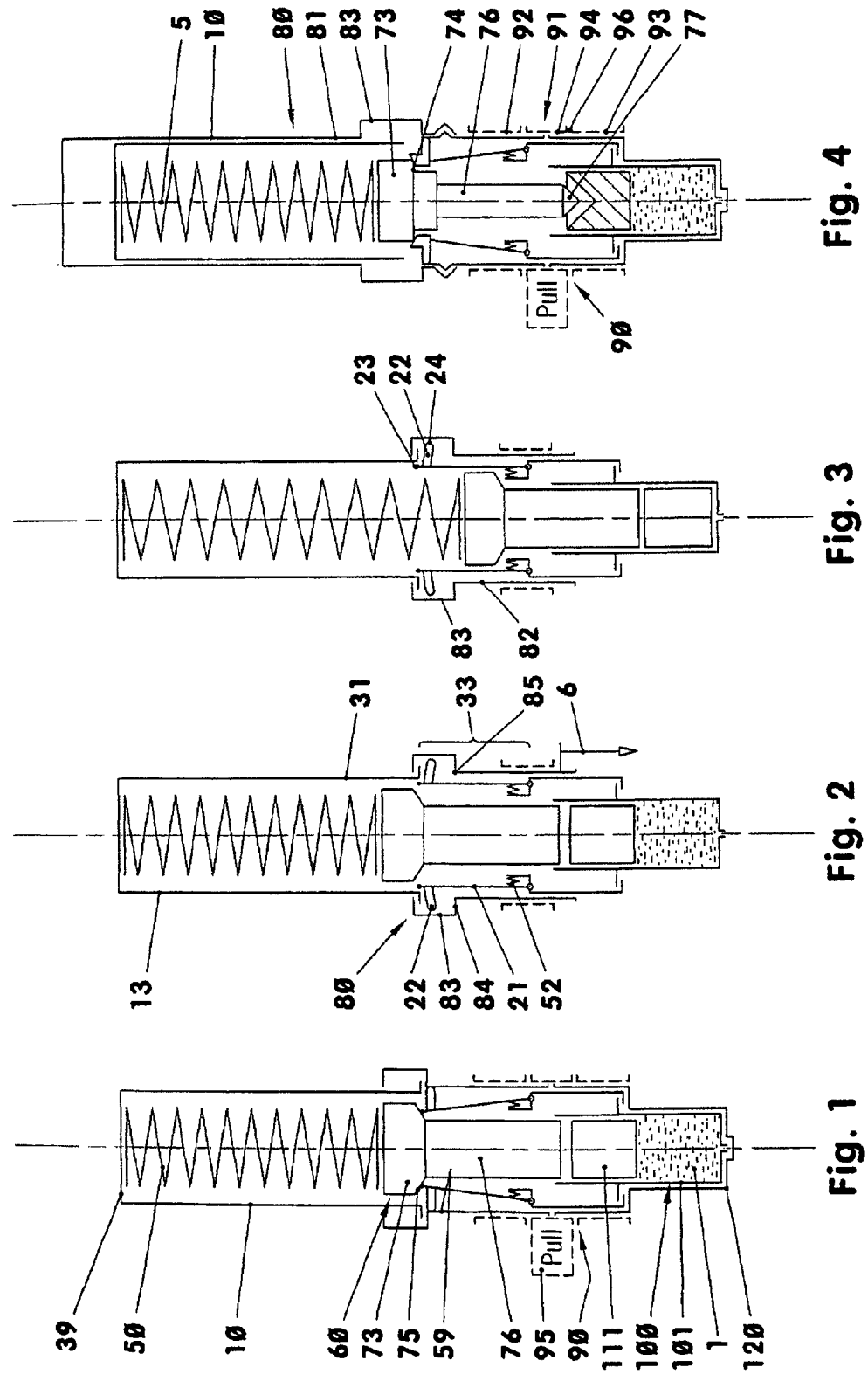

DISPOSABLE INJECTOR WITH AT LEAST ONE COMPRESSION BAR AND A CLOSURE CAP

CROSS-REFERENCE TO RELATED APPLICATION

This is a continuation-in-part application of pending international application PCT/EP2008/004949 filed Jun. 19, 2008 and claiming the priority of German Application No. 10 2007 031 714.1 filed Jul. 6, 2007.

BACKGROUND OF THE INVENTION

The invention relates to a disposable injector with a housing, in which or on which—respectively at least in certain areas—at least one mechanical spring-energy storage, at least one cylinder-piston unit which can be filled at least occasionally with active ingredient, at least one piston-actuating plunger and at least one actuating unit are arranged, whereby the spring-energy storage includes at least one pre-stressed spring-loaded element and whereby at least part of the piston-actuating plunger is positioned between the spring-energy storage and the piston of the cylinder-piston unit.

DE 36 44 984 A1 discloses inter alia such an injector which has a spring pre-stressed piston-actuating plunger, whereof the rearward plunger rod has elastic draw hooks at its free end. The draw hooks hold the piston-actuating plunger positively firmly on one edge of the injector housing. For this they have only minimal bearing surface on the housing. To release the injector the draw hooks are pushed away from the edge holding them. As a result, the spring pre-stressed piston-actuating plunger advances to complete injection.

The object of the present invention is therefore to develop a modular disposable injector which has only a few components for its minimal structural size and guarantees secure mounting and function with easy handling.

SUMMARY OF THE INVENTION

The present invention provides a disposable injector with a housing that has at least one compression hook, which has at least one support surface respectively in the region of its free end. A piston-actuating plunger rests on the support surface. The locking position of the compression hook is secured by an actuating element positioned in a locked position. The actuating element has a locked position, in which it rests securely on a sealing cap. The actuating element has a triggering position, which effects lateral retreat of the compression hook when the piston-actuating plunger is released.

The invention presents here for example a needle-free disposable injector, whereof the piston-actuating plunger is released with a triggering procedure of the disposable injector. For this purpose, for pre-stressing and holding the spring-energy storage the piston-actuating plunger is held positively and non-positively by at least one compression bar arranged on the housing or integrated in the housing. The compression bar or the compression bars is/are held by an actuating element until the disposable injector is used in its locked position and secured by means of a sealing cap which at the same time seals off the cylinder-piston unit as sterile. To trigger the injector the compression bar or the compression bars is/are released so that the piston-actuating plunger can move under the effect of the spring-energy storage at least approximately parallel to the centre line of the disposable injector.

BRIEF DESCRIPTION OF THE DRAWINGS

Further details of the invention will emerge from the following schematically illustrated embodiments, in which:

FIG. 1 illustrates a disposable injector with two compression bars and conical collar surface;

FIG. 2 as for FIG. 1, however unlocked and actuated;

FIG. 3 as for FIG. 2, however following drug ejection;

FIG. 4 illustrates a disposable injector with two support rods and plane front end;

DETAILED DESCRIPTION OF THE PARTICULAR EMBODIMENTS

Figure 5:
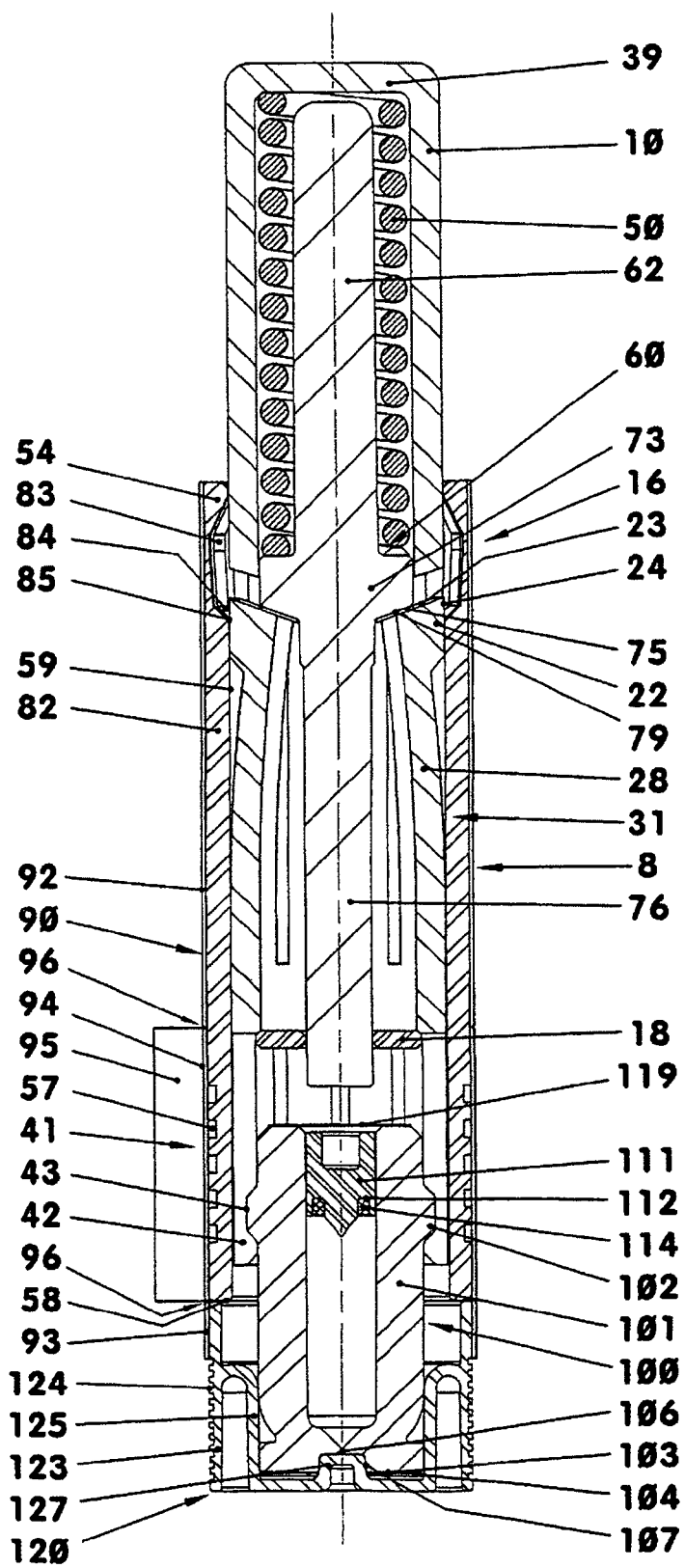
FIG. 5 illustrates a disposable injector with two compression bars deformed in locked position and additionally guided piston-actuating plunger.
Figure 8:
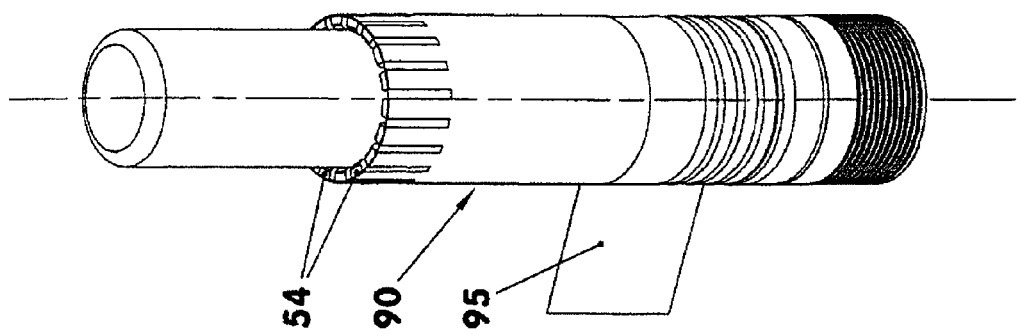
FIG. 8 is a diametrical view of FIG. 5.

FIGS. 1 to 3 show a simplified main sketch of a disposable injector type with permanently loaded spring-energy storage in three different release states. The illustrated disposable injector comprises a housing (10), a cylinder-piston unit (100) pre-filled with e.g. an injection solution, a piston-actuating plunger (60) and a screw compression spring (50) as spring-energy storage. Also, an actuating unit (80) includes an actuating element (82) and a retaining element (90) are arranged on the housing (10). The cylinder-piston unit (100) is sealed from the front by a sealing cap (120). The actuating element (82) in a locked position (8) of the actuating unit (80) rests securely on the sealing cap (120).

The housing (10) is a pot-shaped hollow body, open at the bottom and with an elevated floor (39). The housing (10) has e.g. two opposite window-like openings (33) in the middle region, the shell region (31), as in FIG. 2. Articulated respectively at the lower edge of the single opening (33) is a compression bar or hook (21).

Figure 9:
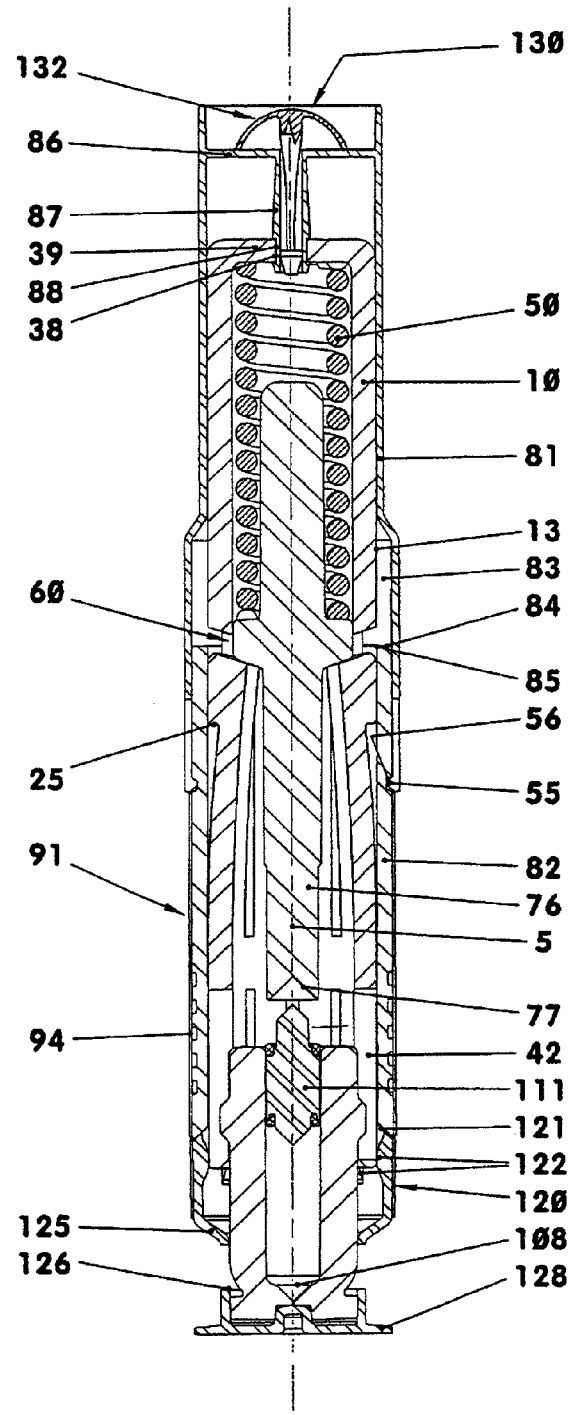
FIG. 9 illustrates a disposable injector with two compression bars deformed in locked position and additional securing.
Figure 14:
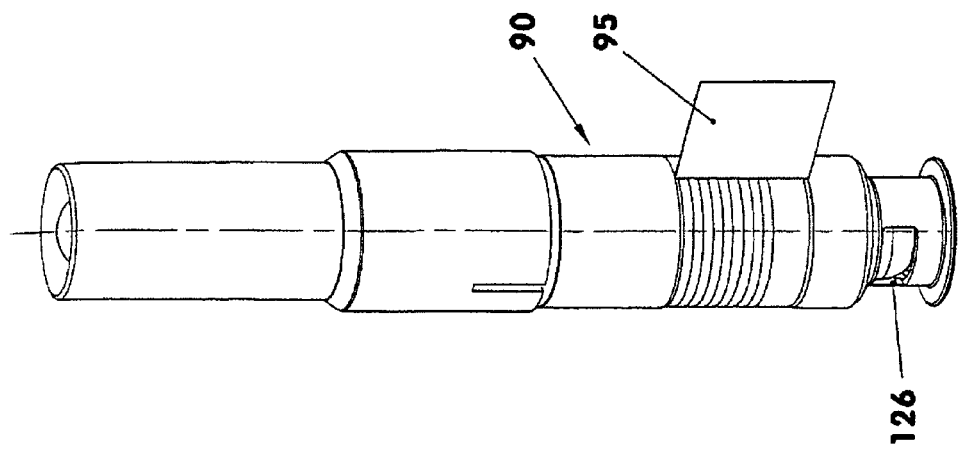
FIG. 14 is a diametrical view of FIG. 9.
Figure 13:
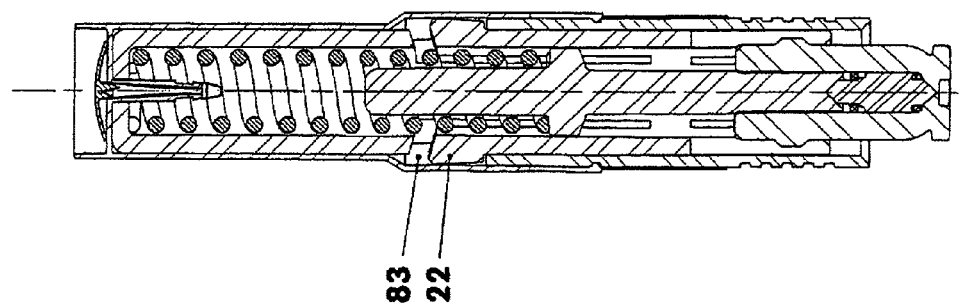
FIG. 13 as for FIG. 12, however with emptied cylinder.
Figure 12:
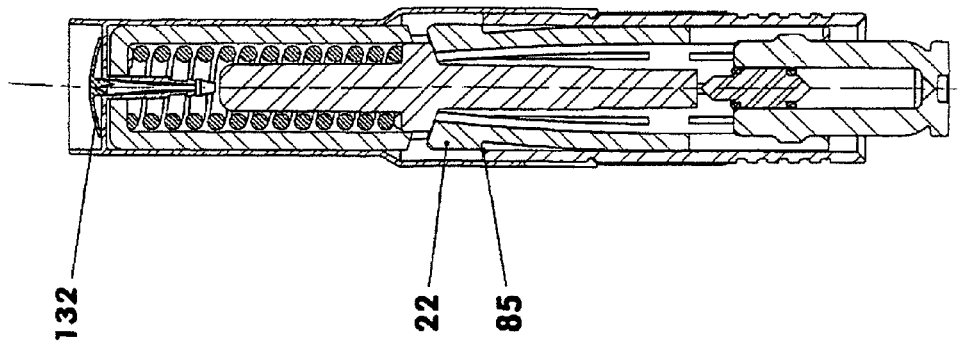
FIG. 12 as for FIG. 9, however unlocked and actuated by removing the banderole (fictitious state)

The compression bars or hooks (21) are arranged here only by way of example in drag-hinges and supported by spring-loaded elements (52) on the housing (10). The spring-loaded elements (52) press the support compression bars or rods (21) at least approximately radially outwards against the actuating element (82), as in FIGS. 1 to 3, where they rest on the actuating element (82) via cams (22). The cams (22) can also lie e.g. 5 to 20 millimeters beneath the respective free upper end of the compression bars (21). If the compression bars (21) are formed on the housing (10), as in FIGS. 5 and 9, they spring outwards as elastic flexional beams (28).

Both pressure-stressed compression bars (21) hold the piston-actuating plunger (60) on its plunger disc (73) in its pre-stressed position, as in FIG. 1. For this purpose, the compression bars (21) are supported on the plunger disc (73) by their support surfaces (23). The size of the respective contact surface between a support surface (23) and the corresponding site on the plunger disc (73) is in the region of 2 to 20 mm$^2$.

On the side averted from the centre line (5) each compression bar (21) has a contact surface (24) on its cam (22).

Located in the lower region of the housing (10) are holders for fastening the cylinder-piston unit (100).

In the embodiment the cylinder-piston unit (100) comprises a transparent cylinder (101) filled with an injection solution (1), in which a piston (111) sits in the rear position. Above the piston (111) in the housing (10) the piston-actuating plunger (60) is e.g. arranged such that although it does not touch the piston, it is guided sideways by its lower end in the upper region of the cylinder (101).

According to FIG. 1 the lower half of the housing (10) is enclosed by the sleeve-like actuating element (82). The actuating element (82) is mounted to move lengthways on the radial outer surface (13) of the housing (10). In this variant, it has a circumferential widened region (83) in the upper region at the level of the cams (22). There can also be partially widened regions or uncovered openings instead of this widened region (83) in the case of a non-rotating symmetrical actuating element (82) per compression bar (21).

The actuating unit (80) has a trigger position (9) which effects lateral retreat of the compression bars (21) when the piston-actuating plunger (60) is released. With respect to the housing (10) the widened region (83) is positioned and dimensioned so precisely that it can take up the outwards-thrust compression bars (21) with their cams (22) retreating during the triggering procedure in the trigger position (9). The inner contour of the widened region (83) is e.g. a channel with a return flank (84), which here represents a plane normal to the centre line (5) of the injector. The transition between for example the cylindrical inner walls of the actuating element (82) and the return flank (84) is configured e.g. as a sharp edge (85). According to FIG. 1 the cams (22) with their outer contact surfaces (24) lie protectively on the inner walls (59) of the actuating element (82).

The piston-actuating plunger (60) arranged in the housing (10) is divided here into two regions. The lower region is the piston slide (76). Its diameter is somewhat smaller than the inner diameter of the cylinder (101) of the cylinder-piston unit (100). The lower front end of the piston slide (76) acts directly on the piston (111).

The upper region, the plunger disc (73), is a flat disc, cylindrical at least in certain areas, whereof the outer diameter is a few tenths of a millimeter smaller than the inner diameter of the housing (10) in the shell region (31). The lower front face (74) has a collar surface (75) arranged around the piston slide (76). It has the shape of a frustoconical surface, whereof the apex angle is about 100 to 130, preferably 120 degree of angle. The notional tip of the frustoconical surface lies on the centre line (5) in the region of the piston slide (76). The collar surface (75) can also be spherically curved.

The piston slide (76) can of course also be designed as a separate component, separate from the plunger disc (73). For this purpose it is located on the inner walls of the housing (10).

The screw compression spring (50) sits pre-stressed between the plunger disc (73) and the superjacent floor (39) of the housing (10). The resilient force is transferred via the plunger disc (73) to the compression bars (21). Due to the inclination of the collar surface (75) the compression bars (21) are thrust radially outwards in the manner of a bevel gear. The release sleeve (82) steadily supports this radial force.

Attached to the lower end of the actuating element (82) is the sealing cap (120) which encloses the lower part of the cylinder-piston unit (100) sterile. Here the sealing cap (120) is mounted on the lower region of the housing (10). The sealing cap (120) and the sleeve-like actuating element (82) are encased at least in certain areas with an adhesive label (91), cf. also FIG. 4. The adhesive label (91) comprises a main part (92), a tear-off banderole (94) and a cap part (93). The tear-off banderole (94) is connected to the label parts (92, 93) by a predetermined breaking point (96), e.g. a perforation or a continuous material thin-point. The tear-off banderole (94) is hereby arranged over the assembly joint laid between the actuating element (82) and the sealing cap (120) and ends in an upright tear-off tab (95).

An all-over adhesive label can also be used, which in the region of the assembly joint separating the parts (82) and (120) contains tearproof pull means. The pull means, e.g. a thread, a plastic strip, a thin wire or the like project to one side over the label. When the pull means are removed the label is specifically undone in the region of the assembly joint.

To activate the injector the tear-off banderole (94) is removed so that the adhesive connection between the sealing cap (120) and the actuating element (82) is broken. After the sealing cap (120) of the cylinder-piston unit (100) is removed the disposable injector is positioned on the injection site to subsequently actuate the disposable injector. The actuating element (82) can now be pushed in the direction of the cylinder-piston unit (100). During this procedure the actuating element (82) slides on the outer wall (13) of the housing (10) downwards and linearly, therefore in the direction of the injection site. The contact surfaces (24) of the compression bars (21) skid over the edge (85) and spring radially outwards in release into the widened region (83) under the force of the spring-loaded element (50). The piston-actuating plunger (60) shoots unhindered downwards, as in FIG. 3. The cylinder (100) is emptied.

A helical movement can also be provided instead of a linear sliding motion of the actuating element (82) on the housing (10). In this case the actuating element (82) and the housing (10) are guided towards one another e.g. via a slide block and a motion link. If required, triggering can also be realized by a pure pivoting movement between the housing (10) and the actuating element (82). The pivot axis here would be the centre line (5).

FIG. 4 shows a variant with a modified actuating unit (80) and another piston slide (76). Attached to the actuating element (82) is an actuating cap (81) which fully encloses the rear end of the housing (10). In the process the actuating cap (81) encompasses the widened region (83).

With this variant the collar surface (74) of the plunger disc (73) is designed flat. The collar surface (74) is oriented normally to the centre line (5). By way of a rounded edge it contacts the upper front ends of the compression bars (21). These front ends are curved in a wedge, truncated or spherical shape. The curving is respectively oriented such that a force acting radially outwards is exerted on the compression bars (21), as for the variant in FIGS. 1 to 3.

Also, the piston slide (76) has a central conical tip (77). This tip (77) projects into a corresponding recess of the piston (111). In this way the piston (111) can also centre and guide the shifted piston-actuating plunger (60) or parts thereof.

FIGS. 5 to 8 show an embodiment of the principle described in FIGS. 1 to 3. Here the load-bearing component is a one-piece housing (10). It is made from e.g. a fibreglass-reinforced polyamide by injection moulding. The housing (10) has an extensively tubular shape and is divided into two functional areas, comprising both the upper shell region (31) and the lower fixing region (41).

The substantially tubular shell region (31) is sealed at the top by an e.g. level floor (39). Located in the lower half of the shell region (31) are two opposite formed-on compression bars (21). The forming-on site for the compression bars (21) is just above the fixing region (41). For forming the respective compression bar (21) there is located in the shell section (31) a narrow, at least approximately U-shaped gap, surrounding the individual compression bar to the sides and at the top. Over about 80% of its length the compression bar (21) has the wall thickness and curve of the walls of the housing (10). This region inter alia also functions as a sprung-elastic flexional beam (28) and has a sickle-shaped cross-section.

Figure 7:
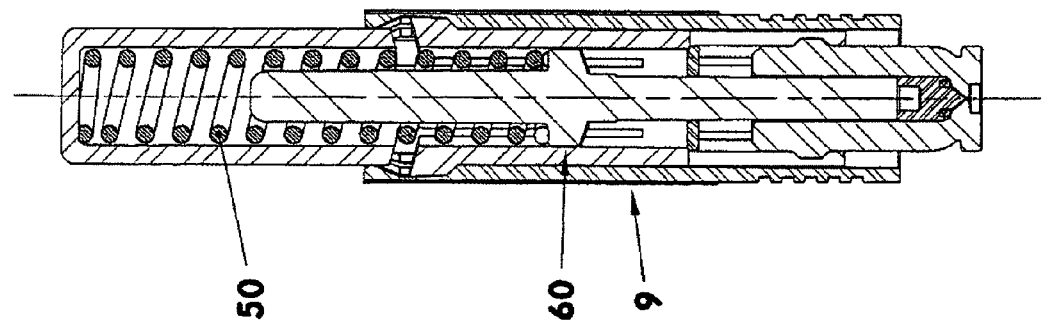
FIG. 7 as for FIG. 6, however with emptied cylinder.
Figure 6:
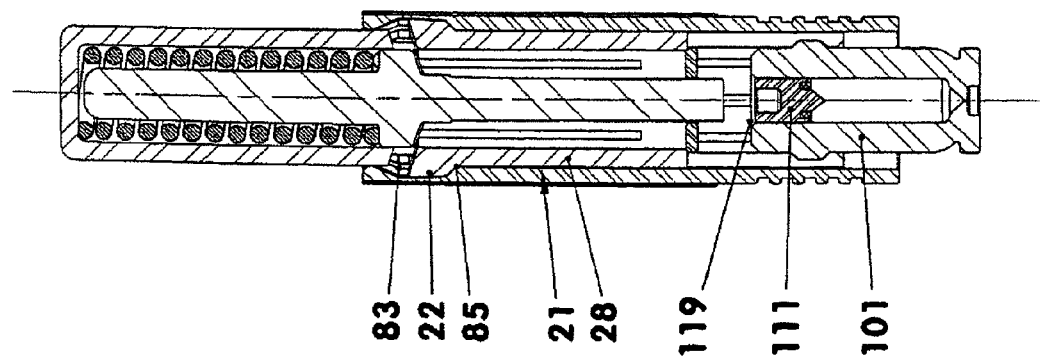
FIG. 6 as for FIG. 5, however unlocked and actuated (fictitious state)

If required, part of this flexional beam (28) can also be equipped with a rectangular cross-section to reduce bending stresses occurring from use in the flexional beam edge region. In FIGS. 6 and 7 the compression bar (21) is shown in the undeformed state.

The upper free end of the individual compression bar (21) is here formed by the radially outwards projecting cam (22), which has at least one support surface (23) and one contact surface (24). According to FIG. 5 the plunger disc (73) of the stressed disposable injector lies on the support surface (23) by its collar surface (75). The support surface (23), here fulfilling the function of a wedged face, has the form of a frustoconical surface with an apex angle of 120 degree of angle.

At least in the contact region the compression bars (21) or the collar surface (75) may have ceramic armouring. In the embodiment in FIG. 5 the collar surface (75) is reinforced by an e.g. stuck-on frustoconical surface-shaped washer (79).

The contact surface (24) of the cam (22) is part of a cylindrical shell, whereof the diameter is e.g. 3 to 4 millimeters larger than the outer diameter of the housing (10). When the disposable injector is stressed the contact surface (24) contacts the inner walls (59) of the sleeve-like actuating element (82). If required, to minimize the surface pressure the contact surface (24) has a curve, which corresponds to the inner walls (59).

Situated under the shell section (31) is the fixing region (41) for taking up the incorporable cylinder-piston unit (100). The fixing region (41) includes e.g. eight spring hooks (42) aligned parallel to the centre line (5). The spring hooks (42) have respectively an at least double-flank rear grip (43) for snugly receiving the cylinder-piston unit (100). The opposing flanks of the rear grip (43) enclose an angle of e.g. 90 degree of angle. The length and the resilient rate of the spring hooks (42) are such that the cylinder (101) can be incorporated without plastic deformation of the spring hooks (42).

The cylinder (101) is e.g. a transparent, thick-walled pot, whereof the cylindrical outer wall bears, for example, a circumferential latching rib (102) where required, which abuts the flanks of the rear grip (43) of the spring hooks (42) dimensionally stably. In the for example cylindrical bore of the cylinder (101) sits the rod-less piston (111). On its at least approximately conical front end the piston (111) has an axial annular groove (112) for receiving a sealing ring (114) or a permanently elastic sealing mass. Set into the rear front end of the piston (111) where required is an e.g. cylindrical metal plate.

Located in the centre of the bore of the cylinder (101), whereof the cylindrical floor matches the contour of the front piston front face at least approximately, is a short cylindrical, nozzle-like bore (106). Its diameter is about 0.1 to 0.5 millimeters. This bore (106) is one to five times as long as its diameter. It ends in a cylindrical recess (107) of the floor-side outer front end (103) of the cylinder (101). This front end (103) can be additionally fitted with an adhesive ring (104) to boost the application safety.

The cylinder (101) is sealed sterile at its end facing the piston slide (76) with a sealing film (119).

Arranged between the piston (111) and the floor (39) is the spring-energy storage (50) or respectively the drive unit of the disposable injector. The spring-energy storage (50) is a screw compression spring, arranged on the piston-actuating plunger (60) with the plunger disc (73). The resilience-stressed piston-actuating plunger (60) is supported on the compression bars (21) of the housing (10) by means of the plunger disc (73).

Above the plunger disc (73) the piston-actuating plunger (60) has a pilot pin (62) which guides the screw compression spring (50). Located centrally under the plunger disc (73) in the extension of the pilot pin (62) is the piston slide (76), which acts on the piston (111) when the disposable injector is actuated. In the embodiment the piston slide (76) ends e.g. 2 to 4 millimeters above the sealing film (119) of the cylinder-piston unit (100).

Arranged in the housing (10) as per FIG. 5 at the upper end of the spring hooks (42) is a perforated guide washer (18), where it sits e.g. clamped in a groove. If necessary, it is also adhered to the housing (10) at this point. The guide washer (18) centres the piston slide (76) in front of the piston (111) of the cylinder-piston unit (100).

The actuating element (82) partially enclosing the housing (10) and the cylinder-piston unit (100) is here likewise a release sleeve. The essentially cylindrical release sleeve (82), e.g. made of ABS, has at its upper end an annular radial widened region (83), which takes up the cams (22) of the compression bars (21) when the disposable injector has been triggered, as in FIGS. 6 and 7. The widened region (83) is formed by a plurality of short spring hooks (54). Here e.g. 18 spring hooks (54) configure the sheathed face of the widened region, as in FIG. 8.

Located in the lower region of the actuating element (82) in its outer walls are several circumferential grooves (57) or another comparable structure. The grooves (57) are e.g. equidistant from one another and extend over 10 to 30 millimeters of the length of the actuating element (82).

A centred sealing cap (120) rests on the lower front end (58) of the actuating element (82) on the cylinder (101) of the cylinder-piston unit (100). Its at least approximately cylindrical outer surface has the same diameter as the likewise cylindrical outer surface of the actuating element (82) in the vicinity of the front face (58).

The sealing cap (120) is a beaker which in a tightly fitting manner encloses the lower quarter of the cylinder-piston unit (100). With its pot area (125) part of the sealing cap (120) surrounds the cylindrical outer walls of the cylinder (101) and the lower front end (103) with the adhesive ring (104) attached there. Formed in the centre of the pot area (125) is a hollow stopper (127), which tightly seals the recess (107). The pot area (125) itself is enclosed by a grip tube (123). The grip tube (123) has on its outer walls creasing (124) or another structure.

The cylindrical actuating element (82) is sheathed over its entire length by an adhesive label (91). The adhesive label (91) itself is e.g. a paper and/or film strip coated on one side by an adhesive in certain areas. In one layer the film strip once surrounds e.g. the compound of sealing cap (120) and actuating element (82). As an original fastener (90) it comprises three separate strips which can be detached towards one another respectively by a perforation (96). The upper strip is the main part (92), the middle strip is a tear-off banderole (94) with a two- to three-centimeter-long tear-off tab (95) and the lower strip is the cap part (93). The main part (92) and the cap part (93) carry an adhesive layer, to which they are attached on the actuating element (82).

To activate the disposable injector the tear-off banderole (94) is separated all around from the main part (92) and from the cap part (93) by means of the tear-off tab (95). The grooves (57) of the actuating element (82) become visible. The sealing cap (120) is now peeled off downwards from the cylinder (101).

The injector is now set onto the injection site and the sleeve-like actuating element (82) pushed downwards in the direction of the injection site. At this point, the cams (22) slip over the edge (85) outwards into the widened region (83). The compression bars (21) bend elastically outwards into their actual starting position. The compression bars (21), no longer deformed, release the piston-actuating plunger (60), as in FIG. 6, so that the piston (111) is suddenly aimed at the sealing film (119) of the cylinder (101) under the effect of the spring-loaded element (50). The sealing film (119) is broken and the piston (111) is moved downwards to empty the cylinder (101), as in FIG. 7.

FIGS. 9 to 14 illustrate a compression bar injector with an actuating unit (80) almost fully enclosing the housing. Attached to the actuating element (82) for this purpose is an actuating cap (81) which encloses the rear end of the housing (10), cf. also FIG. 4. The actuating cap (81) is pushed for this purpose by the rear end of the actuating element (82). This end has as its front end the return flank (84) with the innermost edge (85). Immediately above the return flank (84) in the actuating cap (81) is the widened region (83). The actuating cap (81) rests slidably on the outer walls (13) of the housing (10) above the widened region (83).

For fastening the actuating cap (81) on the actuating element (82), the actuating element (82) has, for example, an annular groove (56), in which a rotational link or detent cam (55) of the actuating cap (81) engages. As in FIGS. 9 and 11 to 14 the actuating cap (81) is e.g. slit longitudinally twice in certain areas for ease of installation.

At the rear end the actuating cap (81) has a sunken cap floor (86). Formed on the cap floor (86) around a centric bore are e.g. several inwards projecting latching tabs (87). At their lower ends the latching tabs (87) respectively have tabbed notches (88) which encompass the edge of a central bore (38) of the housing floor (39).

Figure 10:
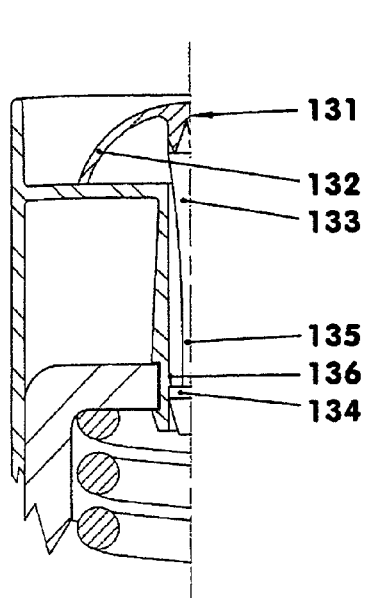
FIG. 10 illustrates a detail enlargement of FIG. 9.

The latching tabs (87) are fixed by a pawl (131) of a pushbutton safety contrivance (130), as in FIG. 10, in the position encompassing the floor (39) in certain areas so that the actuating cap (81) in combination with the actuating element (82) cannot move in a lengthways direction relative to the housing (10).

The pawl (131) has an elastic, partly calotte-shaped pawl knob (132), on which a pawl bolt (133) is formed. The latter bears on its lower free end a blocking collar (134), set down against a waist (135). The blocking collar (134) holds the latching tabs (87) in its locking position, as in FIG. 10, and snaps securely in behind a detent link (136).

If the pawl (131) is actuated by being pressed down the spring-elastic latching tabs (87) spring behind the blocking collar (134) and are applied to the waist (135). The pawl (131) remains permanently in place in its activated position, as in FIGS. 12 and 13. The new sheathed face of the latching tabs (87) now has an outer diameter, smaller than the inner diameter of the bore (38). As a result the mechanical connection between the actuating element (82) and the housing (10) is broken.

Figure 11:
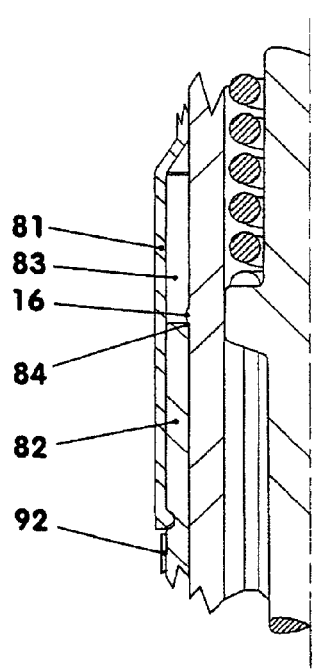
FIG. 11 illustrates a detail enlargement of FIG. 9, however offset by 90 degree of angle.

So as to be able to fix the housing (10) securely together with the spring-loaded element (50) and the piston-actuating plunger (60) in the actuating element (82) during installation, the housing (10) in a region between the cams (22) has a lenticular elevation (16), as in FIG. 11, via which the housing (10) rests on the edge (85) of the actuating element (82).

With the housing (10) illustrated here the support rods (21) have cams (22) with particular rear grip flanks (25). When the support rods (21) are deformed these rear grip flanks (25) lie at least approximately in a plane normal to the centre line (5). When the injector is triggered they accordingly latch abruptly over the edge (85). After triggering they also rest firmly latched on the return flank (84) of the actuating element (82).

The piston-actuating plunger (60) used for this variant has a piston slide (76) with a conical front end (77) bulging inwards, as in FIG. 4 also. With this front end (77) it contacts the conical-shaped tip of the piston (111). Both cones have at least approximately the same cone angle. The illustrated piston (111) is the subject matter of patent DE 10 2006 045 959 C1.

The sealing cap (120) in FIGS. 9 to 12 not only encases the cylinder (101) in certain areas and at the same time rests on the actuating element (82), but also is supported on the housing (10). For this purpose it has in the vicinity of the upper conical front end (121) several contact links (122) arranged on the inner walls, aligned parallel to the centre line (5). The contact links (122) contact the spring hooks (42).

The pot area (125) has two opposing windows (126). The windows (126) have a width which corresponds to at least the diameter of the piston (111). The lower edge of the windows (126)—therefore the edges closest to the washer-like foot (128)—are arranged at the level of the cylindrical floor (108). The density of the cylinder filling can be checked using the windows (126) in the transmitted light inter alia.

In this variant embodiment, with the exception of the spring-loaded element (50), all components can be arranged rotationally symmetrically and/or mirror-symmetrically to a plane laid on the centre line (5).

Using this injector corresponds at least extensively to using the previously described injector variant. But here the additional retaining element (130) is used. After the tear-off banderole (94) is peeled off and the sealing cap (120) removed the injector remains secure. After the injector is set onto the injection site the pawl knob (132) must be pressed e.g. with the thumb of the hand holding the injector for the actuating element (82) to be moved together with the actuating cap (81).

With injectors, in which the piston-actuating plunger (60) is guided straightly in the housing (10)—at least in certain areas—with minimal clearance and the piston-actuating plunger (60) has adequate bending strength, only a single compression bar (21) can be used instead of two or more compression bars (21).

In the variants illustrated in the figures the individual contact zone between the compression bar (21) and the plunger disc (73) is designed as surfaces (23) and (74, 75), which glide on each other on contact. In a particular configuration in each surface (23) of the individual compression bars (21) a roller can be mounted, which rolls away as a roller bearing, therefore almost frictionless, when the injector is actuated on the surface (74, 75) of the plunger disc.

With the exception of the spring-loaded element (50), where required a piston plate and for example the available bearing roller of the support bars (21), all parts of the previously described disposable injectors are made of plastics or plastic- or rubber-like materials.

LIST OF REFERENCE NUMBERS 1 injection solution; drug
5 centre line of the injector, lengthways direction
6 actuation direction of movement of (82), downwards movement directional arrow
8 locked position
9 actuating position, triggering position
10 housing, one-piece
13 outer surface, cylindrical
16 elevation, lenticular
18 guide washer
21 compression rods, support bars
22 cams
23 support surface
24 contact surface
25 rear grip flank
28 flexional beams
31 shell region
33 openings
38 bore
39 floor
41 fixing region for the cylinder-piston unit
42 spring hooks
43 rear grip
50 spring-loaded element, screw compression spring, spring-energy storage
52 spring-loaded elements on (21)
54 spring hooks, short
55 detent cam
56 annular groove of (82)
57 grooves of (82)
58 front end of (82)
59 inner walls of (82)
60 piston-actuating plunger
62 pilot pin
73 plunger disc
74 collar surface, planar
75 collar surface, conical
76 piston slide
77 piston slide front end, conical
79 washer
80 actuating unit
81 actuating cap
82 actuating element
83 widened region
84 return flank
85 edge, sharp-edged
86 cap floor
87 latching tabs
88 tab notches
90 original fastener, banderole, retaining element
91 adhesive label
92 main part of (91)
93 cap part of (91)
94 tear-off banderole
95 tear-off tab
96 perforations, predetermined breaking points
100 cylinder-piston unit
101 cylinder
102 latching rib
103 front end
104 adhesive ring
106 bore, nozzle
107 recess in the front end
108 cylindrical floor
111 piston
112 annular groove
114 sealing ring, seal
119 sealing film
120 sealing cap, adhesive seal
121 front end, top
122 contact links
123 grip tube
124 structure, fluting
125 pot area
126 windows, both sides
127 hollow stopper
128 foot
130 pushbutton safety contrivance, retaining element
131 pawl
132 pawl knob
133 pawl bolt
134 blocking collar
135 waist
136 detent link

What is claimed is:

1. A disposable injector comprising:
a hollow pot-shaped housing (10), in which or on which—respectively at least in certain areas—at least one mechanical spring-energy storage (50), at least one cylinder-piston unit (100) which can be filled at least occasionally with active ingredient, at least one piston-actuating plunger (60) and at least one actuating unit (80) are arranged, the spring-energy storage (50) includes at least one pre-stressed spring-loaded element and at least part of the piston-actuating plunger (60) is positioned between the spring-energy storage (50) and a piston (111) of the cylinder-piston unit (100), the housing has at least one compression bar (21) having a fixed end and a free end, the at least one compression bar (21) either operably affixed to the housing (10) at the fixed end thereof via a spring-loaded element (52) for forcing normally radially outwardly the at least one compression bar (21) at the free end, or formed monolithically as part of the housing (10) and having a sprung-elastic flexional beam (28) which is self-biased in a radially outward direction, the compression bar (21) in the region of its free end having at least one support surface (23),—the piston-actuating plunger (60) rests on the least one support surface (23),—the actuating unit (80) has a locked position (8), the actuating unit (80) in the locked position (8) operatively arranged to laterally secure the at least one compression bar (21),—at least one sealing cap (120) in sterile sealing relationship with the at least one cylinder-piston unit (100), the actuating unit (80) in the locked position (8) in secure resting relationship with sealing cap (120), and—the actuating unit (80) has a triggering position (9), the actuating unit (80) in the triggering position (9) in receptive relationship with the at least one compression bar (21) to effect lateral retreat of the at least one compression bar (21) when the piston-actuating plunger (60) is released.

2. The disposable injector according to claim 1, wherein the piston-actuating plunger (60) has on its front end averted from the spring-energy storage (50) at least in certain areas flat wedged faces or in certain areas single frustoconical faces (74, 75).

3. The disposable injector according to claim 1, wherein together with every single compression bar (21) the piston-actuating plunger (60) forms a spline gear, in which an axial resilient force direction is deflected in a radial support force direction with respect to the housing (10).

4. The disposable injector according to claim 1, wherein every single compression bar (21) is integral with the housing (10) and comprises an elastic flexional beam (28).

5. The disposable injector according to claim 1, wherein the at least one compression bar (21) has at its free end a flat, truncated conical or spherical support surface (23).

6. The disposable injector according to claim 1, wherein actuating unit (80) comprises a releasable sleeve-like actuating unit (82).

7. The disposable injector according to claim 6, wherein the sealing cap (120) is in surrounding relationship with the lower region of the cylinder (101) of the cylinder-piston unit (100), said lower region being fitted with a nozzle (106).

8. The disposable injector according to claim 7, wherein the sealing cap (120) is flush with a lower front end face (58) of the actuating element (82).

9. The disposable injector according to claim 7, wherein the sealing cap (120) is centered on the cylinder (101) of the cylinder-piston unit (100).

10. The disposable injector according to claim 7, wherein in the lower region of the sealing cap (120) further comprises two opposite filling density viewing windows (126).

11. The disposable injector according to claim 10, wherein the windows (126) have a width oriented transversely to the centre line (5) of the injector, which corresponds at least to the diameter of the piston (111) of the cylinder-piston unit (100).

12. The disposable injector according to claim 7, further comprising an original fastener (90), the original fastener (90) in releasable fastened relationship with the actuating element (82) and the sealing cap (120) in the locked position (8) of the actuating unit (80).

13. The disposable injector according to claim 12, wherein the original fastener (90) includes an adhesive label (91) comprising three strips including a tear-off banderole (94), the tear-off banderole (94) is a middle strip arranged in the middle region of the adhesive label (91), the tear-off banderole (94) is operatively connected opposite the remaining two strips of the adhesive label (91) via a perforation (96).

14. The disposable injector according to claim 13, wherein the tear-off banderole (94) operatively covers an assembly joint laid between the actuating element (82) and the sealing cap (120) or borders the latter.

15. The disposable injector according to claim 13, wherein the at least one compression bar (21) has a cam (22) proximate or at the free end thereof.

16. The disposable injector according to claim 15, wherein each compression bar (21) has, on the side averted from the centre line (5) of the injector, a contact surface (24) on its cam (22).

17. The disposable injector according to claim 16, wherein the contact surface (24) of the cam (22), with the actuating unit (80) in the locked position (8), is in constraining contact with the inner wall (59) of the sleeve-like actuating element (82).

18. The disposable injector according to claim 17, wherein the actuating element (82) proximate the upper region thereof has a circumferential widened region (83), with the actuating unit (80) in the trigger position (9), the widened region (83) of the actuating element (82) is operatively positioned to take up the outwards-thrust of the compression bars (21) with their cams (22) retreating into the widened region (83).

19. The disposable injector according to claim 17, wherein the actuating unit (80) further comprises an actuating cap (81) in substantial enclosing relationship with the upper end of the housing (10) proximate the spring-energy storage (50), the actuating cap (81) in attachable arrangement with the actuating element (82).

20. The disposable injector according to claim 19, wherein the actuating cap (81) has a circumferential widened region (83) proximate an innermost edge (85) of actuating element (82), with the actuating unit (80) in the trigger position (9), the widened region (83) of the actuating cap (81) is operatively positioned to take up the outwards-thrust of the compression bars (21) with their cams (22) retreating into the widened region (83).

21. The disposable injector according to claim 19, wherein the actuating cap (81) further includes a sunken cap floor (86), the cap floor proximate a centric bore includes a plurality of inward projecting spring-elastic latching tabs (87) having tabbed notches (88) for engaging housing (10) proximate a central bore (38) of the housing floor (39), a pushbutton safety contrivance (130) including a pawl (131) affixed to each latching tab (87), whereby in the closed position (8) of the actuating unit (80), the actuating cap (81) in combination with the actuating element (82) is prevented from moving in a lengthways direction relative to housing (10).

22. The disposable injector according to claim 21, wherein pawl (131) further comprises a pawl knob (132) having a pawl bolt (133), the pawl bolt (133) at the lower free end thereof having a blocking collar (134), the blocking collar (134) sets down on a waist (135), the blocking collar (134) in restraining relationship whereby in the closed position (8) of the actuating unit (80) with the latching tabs (87) in a locking position prevents the actuating cap (81) in combination with the actuating element (82) from moving in a lengthways direction relative to housing (10), upon the pawl (131) being pressed down the spring elastic latching tabs (87) spring behind blocking collar (134) and are applied to the waist (135), the new sheathed face of the latching tabs (87) is caused to have a smaller diameter then the inner diameter of the bore (38) thus releasing the mechanical connection between the actuating element (82) and the housing (10).

23. The disposable injector according to claim 20, wherein the cams (22) of compression bars (21) have rear grip flanks (25) in operative latching arrangement with the edge (85) of the actuating element (82) when actuation unit (80) is in the triggering position (9).

* * * * *